United States Patent
Barbour et al.

(10) Patent No.: US 7,616,984 B2
(45) Date of Patent: Nov. 10, 2009

(54) MODIFICATION OF THE NORMALIZED DIFFERENCE METHOD FOR REAL-TIME OPTICAL TOMOGRAPHY

(75) Inventors: Randall L. Barbour, Glen Head, NY (US); Yaling Pei, Morris Plains, NJ (US)

(73) Assignees: National Institutes of Health (NIH), Bethesda, MD (US); The United States of America as represented by the Department of Health and Human Services, Washington, DC (US)

( * ) Notice: Subject to any disclaimer, the term of this patent is extended or adjusted under 35 U.S.C. 154(b) by 1156 days.

(21) Appl. No.: 10/408,511

(22) Filed: Apr. 7, 2003

(65) Prior Publication Data

US 2004/0010397 A1    Jan. 15, 2004

Related U.S. Application Data

(60) Provisional application No. 60/370,306, filed on Apr. 6, 2002.

(51) Int. Cl.
*A61B 6/00* (2006.01)

(52) U.S. Cl. .................. 600/473; 600/476; 600/425; 250/332

(58) Field of Classification Search ......... 600/309–344, 600/407, 408, 473–480, 425; 607/1, 88–95; 359/350, 356; 250/330–334, 316.1, 338.1, 250/472.1; 702/189
See application file for complete search history.

(56) References Cited

U.S. PATENT DOCUMENTS 5,137,355 A    8/1992    Barbour et al.

(Continued)

FOREIGN PATENT DOCUMENTS

WO    WO 01/20305 A1    9/2000

(Continued)

OTHER PUBLICATIONS

Kwee, Ivo W. Towards a Bayesian Framework for Optical Tomography. PHD Thesis University of London. 2000. <http://www.medphys.ucl.ac.uk/research/borl/homepages/kwee/thesis_twoside.pdf>.*

(Continued)

*Primary Examiner*—Brian Casler
*Assistant Examiner*—Amanda L. Lauritzen
(74) *Attorney, Agent, or Firm*—Scully, Scott, Murphy & Presser, P.C.

(57)    ABSTRACT

Computation-saving techniques and stability-adding techniques provide for fast, accurate reconstructions of a time series of images involving large-scale 3D problems, such as real-time image recovery in an optical tomography imaging system. A system equation for a target medium (116) such as tissue is solved using a Normalized Difference Method (NDM) (250). Because of the inherent stability of the NDM solutions, a weight matrix (W) of the system equation can be provided for a given point in a time series (220), then reused without recalculation at subsequent points. Further savings are achieved by decomposing W using singular value decomposition or direct matrix decomposition, transforming it to reduce its dimensions, and/or scaling it to achieve a more stable numerical solution. Values of measured energy (112) emerging from the target medium are back-substituted into the system equation for the different points to obtain the target medium properties.

32 Claims, 2 Drawing Sheets

U.S. PATENT DOCUMENTS

| | | | |
|---|---|---|---|
| 5,517,537 A | 5/1996 | Greene et al. | |
| 6,018,562 A | 1/2000 | Willson | |
| 6,078,638 A | 6/2000 | Sauer et al. | |
| 6,081,322 A | 6/2000 | Barbour | |
| 6,529,846 B2 | 3/2003 | Barbour et al. | |
| 6,662,128 B2* | 12/2003 | Barbour et al. | 702/84 |
| 6,795,195 B1* | 9/2004 | Barbour et al. | 356/446 |
| 6,937,884 B1* | 8/2005 | Barbour | 600/473 |
| RE38,800 E* | 9/2005 | Barbour | 600/407 |
| 7,046,832 B1* | 5/2006 | Barbour | 382/131 |
| 7,099,519 B2* | 8/2006 | Barbour et al. | 382/260 |
| 7,142,304 B1* | 11/2006 | Barbour et al. | 356/432 |
| 2003/0059108 A1* | 3/2003 | Hubel | 382/165 |
| 2004/0039268 A1* | 2/2004 | Barbour et al. | 600/310 |
| 2005/0055184 A1* | 3/2005 | Barbour et al. | 703/2 |
| 2006/0018525 A1* | 1/2006 | Barbour | 382/128 |
| 2006/0064001 A1* | 3/2006 | Barbour | 600/407 |
| 2007/0004026 A1* | 1/2007 | Barbour | 435/283.1 |

FOREIGN PATENT DOCUMENTS

| | | |
|---|---|---|
| WO | WO 01/20306 A1 | 9/2000 |
| WO | WO 01/20546 A2 | 9/2000 |
| WO | WO 01/20305 A1 * | 3/2001 |
| WO | WO 01/20306 A1 * | 3/2001 |
| WO | WO 01/20546 A1 * | 3/2001 |

OTHER PUBLICATIONS

A. C. Kak and Malcolm Slaney, Principles of Computerized Tomographic Imaging, IEEE Press, 1988. <http://www.slaney.org/pct/pct-toc.html>.*

* cited by examiner

MODIFICATION OF THE NORMALIZED DIFFERENCE METHOD FOR REAL-TIME OPTICAL TOMOGRAPHY

CROSS-REFERENCE TO RELATED APPLICATIONS

This application claims the benefit of U.S. provisional patent application No. 60/370,306, filed Apr. 6, 2002.

STATEMENT REGARDING FEDERALLY SPONSORED RESEARCH OR DEVELOPMENT

This invention was made with government support under grant 5R21 HL6738701 awarded by the National Institutes of Health. The government has certain rights in the invention.

BACKGROUND OF THE INVENTION

1. Field of the Invention

The invention relates generally to imaging in a scattering medium, and more particularly to a modification of the Normalized Difference Method for solving the perturbation equation associated with a DYnamic Near-infrared Optical Tomography (DYNOT) imaging system, with improved speed and efficiency, to enable image recovery in real time.

2. Description of Related Art

Many techniques and systems have been developed to image the interior structure of a turbid medium through the measurement of energy that becomes scattered upon being introduced into a medium. Typically, a system for imaging based on scattered energy detection includes a source for directing energy into a target medium and a plurality of detectors for measuring the intensity of the scattered energy exiting the target medium at various locations with respect to the source. Based on the measured intensity of the energy exiting the target medium, it is possible to reconstruct an image representing the cross-sectional scattering and/or absorption properties of the target. Exemplary methods and systems were disclosed in Barbour et al., U.S. Pat. No. 5,137,355, entitled "Method of Imaging a Random Medium," the disclosure of which is hereby incorporated by reference for all purposes, and Barbour, U.S. Pat. No. 6,081,322, entitled "NIR Clinical Opti-Scan System" the disclosure of which is hereby incorporated by reference for all purposes.

In particular, DYnamic Near-infrared Optical Tomography (DYNOT) has shown great promise in the field of non-invasive medical imaging. Optical tomography permits the use of near infrared energy as an imaging source. Near infrared energy is highly scattered by human tissue and is therefore an unsuitable source for transmission imaging in human tissue. However, these properties make it a superior imaging source for scattering imaging techniques. The ability to use near infrared energy as an imaging source is of particular interest in clinical medicine because the intensity of the detected energy is exceptionally responsive to blood volume and blood oxygenation levels, thus having great potential for detecting cardiovascular disease, tumors and other disease states.

More recent refinements of these techniques are disclosed in WO 01/20546, published 22 Mar. 2001, "Imaging of Scattering Media Using Relative Detector Values," filed 14 Sep. 2000 as PCT/US00/25156, the disclosure of which is hereby incorporated by reference for all purposes. Therein, a Normalized Difference Method is described that can limit the effect of modeling errors, minimize ill-conditioning of the perturbation equation, and generally stabilize the solution to the image reconstruction problem.

In particular, it was noted that a common approach for the reconstruction of an image of the cross-sectional properties of a scattering medium is to solve a perturbation equation based on the radiation transport equation, which describes the propagation of energy through a scattering medium. The perturbation formulation relates the difference between coefficient values of the true target and a specified reference medium, weighted by a proportionality coefficient whose value depends on, among other things, the source/detector configuration and the optical properties of the medium. Tomographic measurements consider some array of measurement data, thus forming a system of linear equations having the form $$u - u_r \equiv \delta u = W_r \delta x, \qquad (1)$$

where $\delta u$ is the vector of differences between a set of measured light intensities (u) and those predicted for a selected reference medium ($u_r$), $W_r$ is the Jacobian operator, and $\delta x$ is the position-dependent difference between one or more optical properties of the target and reference media (e.g., a change in absorption coefficient, $\delta \mu_a$, a change in the reduced scattering coefficient $\delta \mu'_s$, or, in the diffusion approximation, a change in the diffusion coefficient $\delta D$, where $D=1/[3(\mu_a + \mu'_s)]$. The operator, referred to as the weight matrix, has coefficient values that physically represent the fractional change in light intensity at the surface caused by an incremental change in the optical properties at a specified point in the medium. Mathematically, this is represented by the partial differential operator $\partial u_i / \partial x_j$, where i refers to the $i^{th}$ source/detector pair at the surface of the medium, and j to the $j^{th}$ pixel or element in the medium.

Although the perturbation equation in Eq. (1) can be solved using any of a number of available inversion schemes, the accuracy and reliability of the results obtained can vary greatly due to uncertainties and errors associated with the quality of the measurement data, inaccuracies in the physical model describing light propagation in tissue, specification of an insufficiently accurate reference state, the existence of an inherently underdetermined state caused by insufficiently dense measurement sets, weak spatial gradients in the weight function, and so forth.

A matter of considerable concern is the accuracy with which the reference medium can be chosen. An accurate reference is one that closely matches the external geometry of the target medium, has the same size, nearly the same internal composition, and for which the locations of the measuring probes and their efficiency coincide well with those used in the actual measurements. While such conditions may be easily met in numerical simulations, and perhaps also in laboratory phantom studies, they represent a much greater challenge in the case of tissue studies. Confounding factors include the plasticity of tissue (which deforms upon probe contact), its mainly arbitrary external geometry and internal composition, and the considerable uncertainty stemming from the expected variable coupling efficiency of light at the tissue surface. The influence of these uncertainties can be appreciated when it is recognized that the input data vector for the standard perturbation formulation (i.e., Eq. (1)) is actually the difference between a measured and a computed quantity. This vector contains information regarding the subsurface properties of the target medium that, in principle, can be extracted provided an accurate reference medium is available.

However, there are two significant concerns that are frequently encountered in experimental studies and are not easily resolvable, especially in the case of tissue studies. One concern is the expected variable coupling efficiency of light entering and exiting tissue. Nonuniformity in the tissue surface, the presence of hair or other blemishes, its variable deformation upon contact with optical fibers, and the expected variable reactivity of the vasculature in the vicinity of the measuring probe all serve to limit the ability to accurately determine the in-coupling and out-coupling efficiencies of the penetrating energy. Variations in the coupling efficiency will be interpreted by the reconstruction methods as variations in properties of the target medium and can introduce gross distortions in the recovered images. The noted concern can be minimized by adopting absolute calibration schemes; however, the variability in tissue surface qualities will limit reliability and stability of these efforts.

A second concern stems from the underlying physics of energy transport in highly scattering media. One effect of scattering is to greatly increase the pathlength of the propagating energy. Small changes in the absorption or scattering properties of the medium can, depending on the distance separating the source and detector, greatly influence the intensity of emerging energy. This consideration has important implications for the required accuracy with which the reference medium must be specified. In the context of perturbation formulations, the reference medium serves to provide predictions of the measured energy intensities and also provides the needed weight functions that serve as the imaging operators. The difficulty is that the computed reference intensities are extremely dependent on the optical coefficient values of the reference medium. Significantly, this dependence is a nonlinear function of the distance between source and detector. It follows that a small change in the optical properties of the reference medium may influence the value of the computed intensity differences ($\delta u$) by a relative amount that may be significantly different for each source/detector pair, thereby altering the information content of the data vectors. This can lead to the recovery of grossly corrupted images. While in principle such effects may be overcome by use of recursive solutions to the perturbation equation (i.e., Newton-type updates), in practice this can require extensive computational efforts, especially in the case of 3D solutions. Moreover, such efforts to improve on first-order solutions to the perturbation equation (e.g., Born or Rytov solutions), can fail if the initial estimate chosen for the reference medium is insufficiently accurate.

WO 01/20546 addressed the need for image reconstruction techniques based on the detection of scattered energy that (1) do not require absolute calibration of, and absolute measurements by, the detectors and other elements of the apparatus, (2) make the standard perturbation equation less susceptible to variations between boundary conditions and properties of the reference medium and the target medium, and (3) produce solutions having physical units.

It was noted that the typical process for imaging of a scattering medium comprises: (1) selecting a reference medium having known boundary conditions and optical properties which are substantially similar to those of the intended target; (2) determining a weight matrix and an intensity of emerging energy exiting the reference medium at each of a plurality of source points for each of a plurality of detectors located around the reference medium boundary, the determination being made by either actual measurements or solution of the radiation transport equation or an approximation thereto; (3) measuring actual emerging energy intensities for corresponding source and detector points on a target medium; and (4) solving the perturbation equation for the optical properties of the target based on the measured intensities of energy emerging from the target.

WO 01/20546 described an improved methodology for imaging of a scattering medium using a modified form of the standard perturbation equation, which was capable of (1) reducing the sensitivity of the perturbation equation to differences between the reference medium and target medium, (2) producing solutions to the perturbation equation having physical units, and (3) reducing the effect of variable detector efficiencies without the need for absolute calibration, while at the same time preserving the ability to compute recursive solutions. Compared to the standard perturbation approach, the described approach provided a remarkable improvement in the quality of image reconstruction.

While the method was applicable to known static imaging techniques, it was also instrumental in the realization of practical dynamic imaging of highly scattering media. A first element of dynamic imaging is the development of a fast, parallel, multi-channel acquisition system that employs geometrically adaptive measuring heads. This system is described in further detail in PCT/US00/25155, published on Mar. 22, 2001 as WO 01/20306, incorporated herein by reference. The second element is to evaluate the acquired tomographic data using the modified perturbation methods of the present invention. The third element is to collect a time series of data and subject either the time series of data or a time series of images reconstructed from the data to analysis using various linear and nonlinear time-series analysis methods to extract dynamic information and isolated dynamic information. These methods are described in further detail in PCT/US00/25136, published on Mar. 22, 2001 as WO 01/20305, incorporated herein by reference.

Some of the methods, systems and experimental results described focused on optical tomography of human tissue using wavelengths in the near infrared region for the imaging source. The techniques were generally applicable to the use of essentially any energy source (e.g., electromagnetic, acoustic, and the like) on any scattering medium (e.g., body tissues, oceans, foggy atmospheres, earth strata, industrial materials) so long as diffusive-type mechanisms are the principal means for energy transport through the medium.

Figure 1:
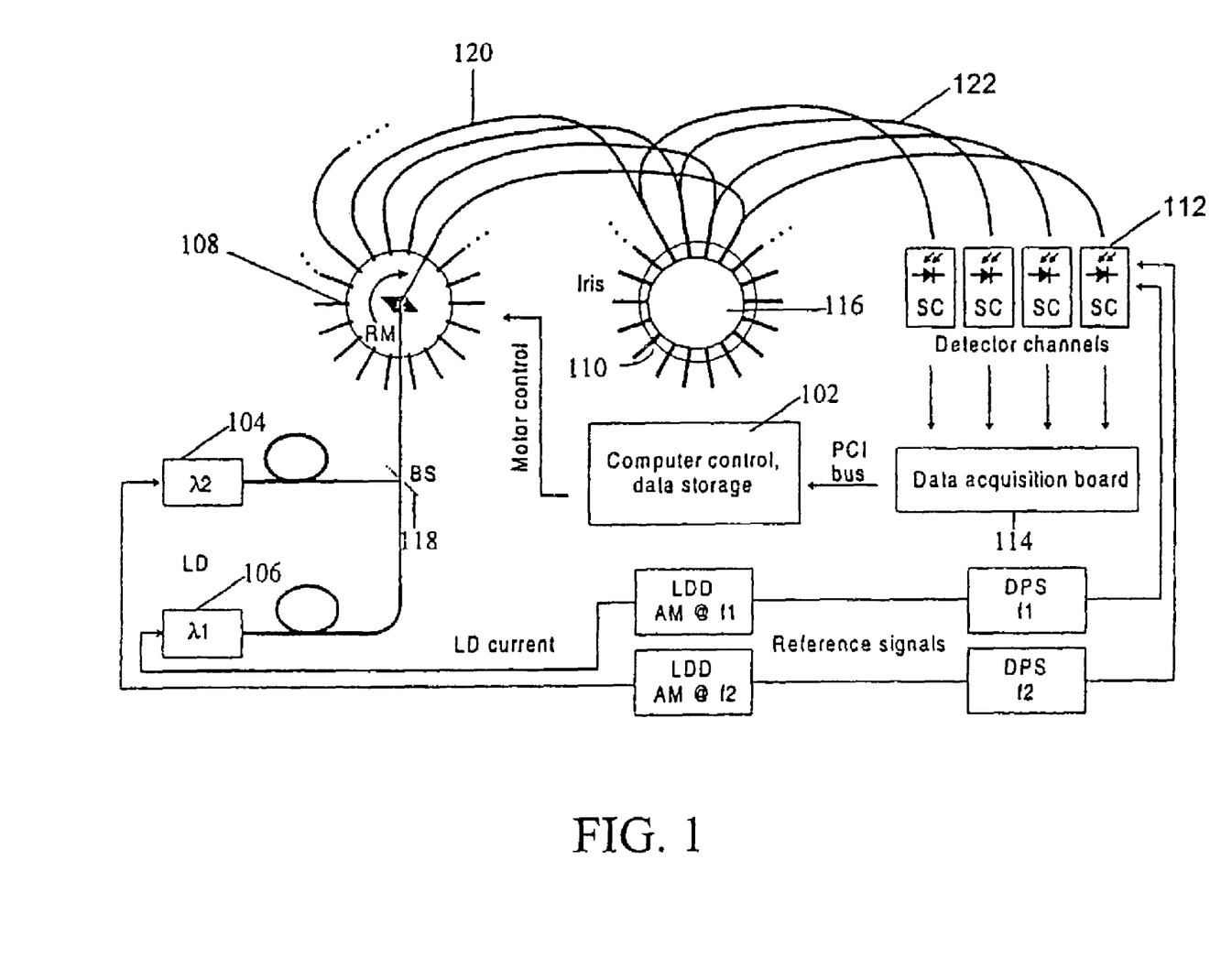
FIG. 1 is a schematic illustration of an exemplary imaging system.

Numerous imaging systems such as those disclosed in the previously mentioned Barbour '355 patent and the Barbour '322 patent have been developed for use in imaging of a scattering medium. A schematic illustration of an exemplary system is shown in FIG. 1. This system includes a computer 102, sources 104, 106, a source demultiplexer 108, an imaging head 110, detectors 112 and a data acquisition board 114. A target 116 placed in the imaging head 110 is exposed to optical energy from sources 104,106. The optical energy originating from sources 104,106, is combined by beam splitter 118 and is delivered to source demultiplexer 108. The source demultiplexer 108 is controlled by computer 102 to direct the optical energy to source fibers 120 sequentially.

Each source fiber 120 carries the optical energy from the demultiplexer 108 to the imaging head 110, where the optical energy is directed into the target 116. The imaging head 110 contains a plurality of source fibers 120 and detector fibers 122 for transmitting and receiving light energy, respectively. Each source fiber 120 forms a source-detector pair with each detector fiber 122 in the imaging head 110 to create a plurality of source-detector pairs. The optical energy entering the target 116 at one location is scattered and may emerge at any location around the target 116. The emerging optical energy is collected by detector fibers 122 mounted in the imaging head 110.

The detector fibers 122 carry the emerging energy to detectors 112, such as photodiodes or a CCD array, that measure the intensity of the optical energy and deliver a corresponding signal to a data acquisition board 114. The data acquisition board 114, in turn, delivers the data to computer 102. The computer 102 processes values of the measured energy for use in solving the system equation for the target medium. This imaging process is repeated so as to deliver optical energy to each of the source fibers sequentially, a measurement being obtained for detected emerging energy at each detector for each emitting source fiber. This process may continue over a period of time with the computer 102 storing the data for reconstruction of one or more images. Additionally, the system may include two or more imaging heads for comparing one target to another. The computer 102 reconstructs an image representative of the internal optical properties of the target by solving a perturbation equation. It will be appreciated by those skilled in the art that more than one computer can be used to increase data handling and image processing speeds.

The Standard Perturbation Formulation

As discussed above, reconstruction of a cross-sectional image of the absorption and/or scattering properties of the target medium is based on the solution of a perturbation formulation of either the radiation transport equation or the diffusion equation. The perturbation method assumes that the composition of the unknown target medium deviates by only a small amount from a known reference medium. This reduces a highly nonlinear problem to one that is linear with respect to the difference in absorption and scattering properties between the target medium under investigation and the reference medium. The resulting standard perturbation equation has the form of Eq. (1), discussed above, where $\delta u$ is a vector of source-detector pair intensity differences between the measured target medium and the known reference medium (i.e., $\delta u = u - u_r$). W is the weight matrix describing the influence that each volume element ("voxel") of the reference medium has on energy traveling from each source to each detector, for all source-detector pairs. The volume elements are formed by dividing a slice of the reference medium into an imaginary grid of contiguous, non-overlapping pieces or sections. Physically, the weight matrix contains the first-order partial derivatives of the detector responses with respect to the optical coefficients of each volume element of the reference medium. $\delta x$ is the vector of differences between the known optical properties (e.g., absorption and scattering coefficients) of each volume element of the reference medium and the corresponding unknown optical properties of each volume element of the target medium.

This standard perturbation equation assumes (1) use of absolute detector measurements for u, and (2) that the boundary conditions and optical properties of the reference do not vary significantly from those of the target. Both of these factors are problematic in practice.

The Modified Perturbation Formulation

WO 01/20546 discussed modifying the standard perturbation equation by replacing $\delta u$ with a proportionate relative difference between two measured values multiplied by a reference term with the required units as set forth in the equation (2) below:

$$(\delta I_r)_i = \left[\frac{I_i - (I_0)_i}{(I_0)_i}\right](I_r)_i \quad (2)$$

where i is the source/detector pair index. In equation (2), $I_r$ is the computed detector reading corresponding to a source-detector pair of a selected reference medium, and I and $I_0$ represent two data measurements for a corresponding source-detector pair on one or more targets (e.g., background vs. target, or time-averaged mean vs. a specific time point, etc.). The resultant term $\delta I_r$ therefore represents a relative difference between two sets of measured data that is then mapped onto a reference medium. This modification has important attributes that limit the effects of modeling errors and minimize ill-conditioning of the inverse problem (i.e., image reconstruction problem), while retaining the correct units in the solution.

The corresponding perturbation equation using this modified term is:

$$W_r \cdot \delta x = \delta I_r \quad (3)$$

In equation (3) $W_r$ and $\delta x$ are the same as $W_r$ and $\delta u$ in equation (1). Referring to equations (2) and (3), it can be seen that in the limit, when $I_r$ equals to $I_0$, this equation reduces to the standard perturbation formulation shown in equation (1). This formulation represents the Born approximation formulation of the modified perturbation equation. A similar expression may be written for the Rytov approximation in the following form:

$$(\delta I')_i = \ln\frac{I_i}{(I_0)_i};$$

$$(W'_r) = \frac{(W_r)_{ij}}{(I_r)_i};$$

$$\delta I' = W'_r \delta x \quad (4)$$

Equation (2) preserves the information content of a measured proportionate relative data vector obtained from the target medium and yields data vector having the correct physical units. Apart from simplifying measurement requirements, the method represented by equations (3) and (4) also reduces susceptibility of the perturbation equation to boundary and optical property variations between the target and the reference media. Additionally, iterative solutions of equations (3) and (4) can be easily implemented. In principle, the techniques used in the modified perturbation equation, referred to as the normalized difference method (NDM), can be used to evaluate any measured proportionate relative quantity.

Experimental Validation

WO 01/20546 presented examples that illustrate the benefits of applying the NDM approach for the analysis of relative measures from highly scattering media.

Forward Model and Data Acquisition Geometry

For any intended target, the perturbation equation is generated for a reference medium having boundary conditions and optical properties substantially similar to the target. The perturbation equation models the energy propagation, e.g., light, in the reference medium as a diffusion process. For a domain $\Omega$ having a boundary $\delta\Omega$ this is represented by the expression $$\nabla \cdot [D(r)\nabla u(r)] - \mu_a(r)u(r) = \delta(r-r_s), r\in\Omega \quad (5)$$

where u(r) is the photon density at position r, $r_s$ is the position of a DC point source, and D(r) and $\mu_a(r)$ are the position-dependent diffusion and absorption coefficients, respectively. The diffusion coefficient is defined as $$D = 1/\{3[\mu_a(r) + \mu'_s(r)]\} \quad (6)$$

where $\mu'_s(r)$ is the reduced scattering coefficient. The photon density values at the detectors, i.e., the calculated intensity of energy emerging from the reference medium at each detector, were computed by applying Dirichlet boundary conditions on an extrapolated boundary. Depending on the target medium to be explored, sources and detectors for the reference are positioned 1 to 2 transport mean free pathlengths within the boundary of the reference medium.

Solutions to the diffusion equation may be computed by any known means, such as by the KASKADE adaptive finite element method [R. Beck, R. Erdmann and R. Roitzsch, "Kaskade 3.0—An object-oriented adaptive finite element code," Technical report TR 95-4, Konrad-Zuse-Zentrum fur Informationstechnik, Berlin (1995)]. This is a publicly available code suitable for the solution of partial differential equations in one, two or three dimensions using adaptive finite element techniques. The code can be readily modified to permit solutions to the diffusion equation using a point source. Mesh generation may be by any known method, such as the Delaunay tessellation algorithm originally described by Watson [D. F. Watson, "Computing the n-dimensional Delaunay tessellation with applications to Voronoi polytopes", Computer Journal, 24,167-172 (1981)].

The perturbation equation is specific to the boundary conditions and optical properties of the reference medium, including the orientation of the source-detector pairs in relation to one another and to the reference medium. These conditions and properties are preferably nearly identical to those of the target. For example, in the experiments discussed below, the perturbation equation was generated based on an imaging system having six sources and eighteen detectors per source (108 source-detector pairs) with the sources equally spaced at 60 degree intervals around the boundary of the medium and the detectors equally spaced at 20 degree intervals.

Inverse Algorithm

As described above, the relative intensities are measured for all source-detector pairs using any known imaging system. Image recovery is then achieved using known methods, such as conjugate gradient descent (CGD), or simultaneous algebraic reconstruction techniques (SART), to solve the modified perturbation equation for the absorption and scattering properties of the target. See J. Chang, H. L. Graber, R. L. Barbour and R. Aronson, "Recovery of optical cross-section perturbations in dense-scattering media by transport-theory-based imaging operators and steady-state simulated data", Appl. Opt. 35, 3963-3978, (1996) (the disclosure of which is incorporated herein by reference). For example, the experimental results discussed below were achieved using a CGD solver, both with and without matrix rescaling. In addition, a weight matrix rescaling (WMR) technique may be used to improve the conditioning of the weight matrix. The effect of rescaling the weight matrix is to make it more uniform. Two rescaling criteria can be applied for this purpose: (1) rescaling the maximum of each column to 1; or (2) rescaling the average of each column to 1. When WMR was used, criterion (1) was applied for image recovery. The solution to the modified perturbation equation provides a relative measure of the difference between the cross-sectional optical properties of a target during the first and second measurements I and $I_0$. The values from this solution are used to generate cross-sectional images representative of the target's internal optical properties.

Building upon the above knowledge, the present invention modifies the Normalized Difference Method to enable real-time image recovery in a tomography or other imaging system. Because of the inherent stability of solutions obtained from the Normalized Difference Method, a variety of computation-saving techniques and stability-enhancing techniques are introduced to provide fast, accurate reconstruction of a time series of images involving large-scale 3D problems.

BRIEF SUMMARY OF THE INVENTION

The present invention includes a method of real-time tomography of a turbid, scattering target medium. In a method of the invention, a reference medium is selected having generally known boundary conditions and optical properties that are substantially similar to those of the target medium. Energy may originate within the target medium, and/or be emitted into the region by an energy source. A weight matrix describes the spatial distribution of detected light or other energy exiting the reference medium at each of a plurality of detectors, for each of a plurality of source points located around the reference medium boundary, when point sources are used. The energy emitted by each source point is typically detected by a number of detectors. The actual intensities of emerging energy for the corresponding source and detector points on the target medium is measured. A matrix decomposition and back-substitution method is employed to solve the perturbation equation, thereby determining the optical properties of the target medium based on said measured intensities of energy emerging from the target medium. To create time-series information about the target medium, a back-substitution is performed with subsequently measured data in the decomposed matrix. A matrix transform technique may be used to limit the dimensions, e.g., size, of the matrix to be solved prior to the matrix decomposition step. Moreover, prior to matrix decomposition and particularly back-substitution, the measured intensities may be normalized over either time or space, achieving a more stable numerical solution.

In a particular embodiment, a method is provided for obtaining a time series of tomographic images of a target medium, wherein source-detector pairs are positioned about a boundary of the target medium, and, in each source-detector pair, for different points in the time series, the source emits energy into the target medium and the detector measures the energy emerging from the target medium after passage therethrough. The method includes selecting a reference medium and providing a weight matrix describing the influence that volume elements of the reference medium have on energy traveling from sources to detectors in source-detector pairs of the reference medium. For the different points in the time series, the method further includes solving a system equation for the target medium to determine properties of volume elements of the target medium corresponding to the volume elements of the reference medium based on the weight matrix and the energy emerging at the detectors of the target medium.

In a further particular embodiment, a method for obtaining a time series of images of a target medium includes positioning detectors about a boundary of the target medium for measuring energy that emerges from the target medium at different points in the time series, wherein the energy originates within the target medium rather than being emitted into the target medium by an energy source. The method further includes selecting a reference medium and providing a weight matrix describing the influence that volume elements of the reference medium have on energy originating within the reference medium and emerging from the reference medium at detectors positioned about a boundary of the reference medium. For the different points in the time series, the method further includes solving a system equation for the target medium to determine properties of volume elements of the target medium corresponding to the volume elements of the reference medium based on the weight matrix and the energy emerging at the detectors of the target medium.

BRIEF DESCRIPTION OF THE FIGURES

For a better understanding of the invention, together with the various features and advantages thereof, reference should be made to the following detailed description of the preferred embodiments and to the accompanying drawings wherein.

DETAILED DESCRIPTION OF THE INVENTION

As described above, the Normalized Difference Method for optical tomography provides for highly stable solutions to the image reconstruction problem. The present invention extends this formulation to provide for real-time image recovery in cases where a time series of images is being considered.

It is well known that time-variable characteristics of tissue under investigation, for example a vascular bed, are invaluable in identifying reliable indications of the state of the tissue. When using a DYNOT system for diagnostic purposes, two problems arise. First, the global changes in the target tissue can mask characteristics of interest if not properly accounted for. To strictly account for these global variations would require a reference medium that varies in time to model the changes, vastly increasing computational overhead. A second, related problem is that computations required for image generation according to the general solution of the perturbation equation are far too cumbersome to be accomplished in real time, even by modem standards. The present invention is a solution to the latter problem that is enabled by our solution to the former.

In our prior disclosure WO 01/20546, we introduced the Normalized Difference Method. This minimized the sensitivity of the image solution against the deleterious effects of an insufficiently accurate reference medium. A key element of the formulation of the present invention is to recognize that, because of the stability of the Normalized Difference Method, one is now able to apply the same reference medium to all images in the time series without loss of image acuity. Having a stable solution in the time dimension, for example, allows for the application of matrix decomposition methods, such as singular value decomposition (SVD), direct matrix decomposition or other techniques, wherein it is sufficient to compute the singular values and corresponding singular vectors associated with the matrix of the system equation only once. Thereafter, one can back-substitute the detector values for each successive time point to yield the image time series. This has the effect of reducing a normally $N^3$ problem to an $N^2$ problem, where N is equal to twice the number of nodes defining a finite element mesh which models the target tissue. This reduction greatly reduces required computing times. As normally applied, the SVD algorithm has the added benefit of allowing for truncation of the singular value spectrum, thereby further improving the stability of the solution.

While this approach is effective, it can be further shown that, especially in the case of 3D problems, the computing time necessary to decompose the matrix of the final system equation, even once, can still be considerable. This problem can be addressed by introducing a matrix transform method that has been successfully applied to other problems. The essence of the matrix transform method is to recognize that the weight function itself can serve as a basis function for a transformed representation of the original unknowns. In this manner, transformation of the system equation $$W\delta x = \delta u \qquad (7)$$

where W is the weight function matrix, $\delta u$ is the attenuation coefficient, i.e., some measure of the difference between an expected intensity and a measured intensity, and $\delta x$ is the property change under investigation, is accomplished by use of the transpose of the weight function W itself as the basis, i.e., $W^T = [W_1^T W_2^T \ldots W_M^T]$. Therefore, the unknowns $\delta x$ in a system equation using the Normalized Difference Method can be spanned as $$\delta x = \sum_{k=1}^{M} w_k^T \cdot \delta \tilde{x}_k = W^T \cdot \delta \tilde{x}.$$

This formulation results in the transformed system equation $A \cdot \delta \tilde{x} = \delta u$, where $A = W \cdot W^T$. Solution of this transformed system equation yields the following intermediate solution and final solutions, $$\delta \tilde{x} = A^{-1} \cdot \delta u \qquad \text{and} \quad \delta x = W^T \cdot A^{-1} \cdot \delta u \qquad \text{(8a and 8b)}$$
$$= [W \cdot W^T]^{-1} \cdot \delta u \qquad = W^T \cdot [W \cdot W^T]^{-1} \cdot \delta u$$

respectively. Here, the symbols W and $\delta x$ are defined as representing the weight matrix and the unknowns, respectively.

We define $(\delta u)_i = \{[(u_1)_i - (u_2)_i]/(u_2)_i\}(u_i)$ with $i=1,2,\ldots,M$, as representing the normalized difference data vector, where u is the computed detector readings corresponding to the selected reference medium, $u_2$ and $u_1$ represent two sets of measured data, for example time-averaged mean and a specific time point, respectively, and M is the number of source-detector pairs in the set of measurements.

The effect of employing the weight transformation technique is to reduce the normally large M×N matrix, where, again, N is the twice the number of nodes comprising the finite element mesh, to a much smaller M×M matrix. This transformation will considerably reduce the required computing time, in particular for large 3D problems.

Further, improved stability to these solutions can be achieved by introducing appropriate scaling methods applied to the weight matrix. The motivation for this comes from our recognition that the range of values in the unscaled Jacobian can be very large, rendering the problem ill-conditioned. Several approaches can be applied. In one example, the mean value of each row vector of the Jacobian can be normalized to unity. Alternatively, a similar normalization can be applied to the maximum value for each row. Still other normalizations of the weight matrix can be considered that apply some smoothly varying function in concert with the separation distance between any source and detector. As we have previously disclosed, scaling of the column vectors can be applied as well.

Figure 2:
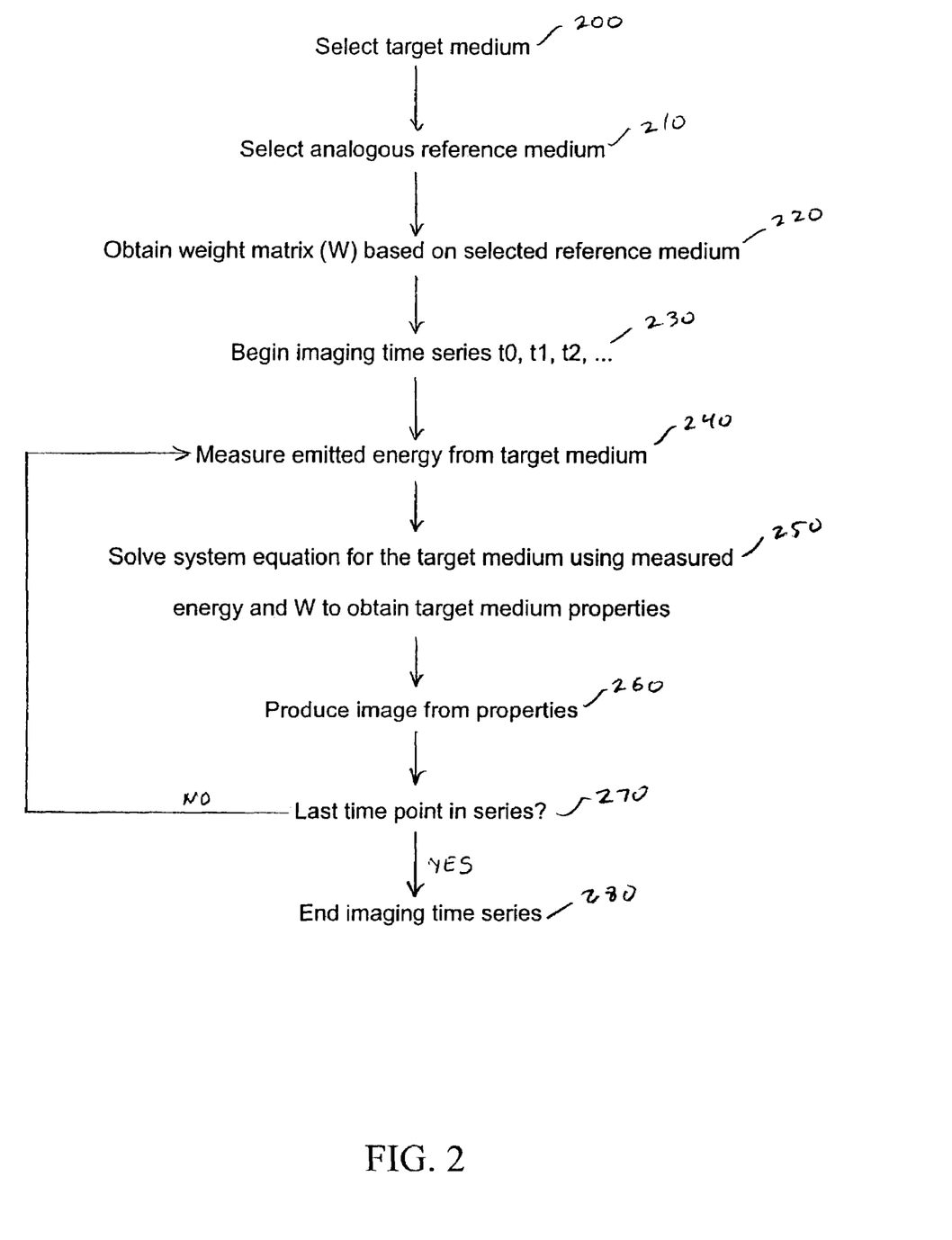
FIG. 2 illustrates a method for calculating properties of a target medium according to the invention.

FIG. 2 illustrates a method for calculating properties of a target medium according to the invention. At block 200, a target medium is selected, and at block 210, an analogous reference medium is selected. At block 220, a weight matrix is obtained based on the selected reference medium. For example, the weight matrix may be obtained from a storage area in a computer memory of weight matrices that are correlated with different reference media. For instance, when the target medium comprises a human breast that is being imaged to detect cancer, a library of weight matrices may be determined ahead of time, e.g., before the imaging of the target medium, based on different breast sizes and shapes. These weight matrices may be developed from averages of measurements made of a number of healthy volunteer subjects, for instance. The human breast that is being imaged as the target medium can be measured to determine which of the reference media in the library is most analogous, e.g., as far as boundary shape and conditions, and internal tissue structure. The weight matrix for that reference medium can then be retrieved, e.g., by reading the weight matrix data from a long term memory, such as a hard disk, into a short term memory, such as RAM, in a computer. Or, a reference medium which is estimated to correspond to the target medium may be used. Thus, the weight matrix for the reference medium generally will be estimated.

In one option, the target medium and reference medium include analogous tissue regions in an animal such as a human. For example, the reference medium may be from a healthy breast, while the target medium is from the contralateral breast of the same subject that is suspected to have a tumor. In this case, an initial estimated reference medium with weight matrix is provided, and energy measurements are made from the healthy breast as the target medium to determine a weight matrix of the healthy breast. The healthy breast, with its associated weight matrix, is then used as a reference medium to determine properties of the suspected unhealthy breast. The analogous tissue regions may also include different portions of the same breast, for instance. Various other tissue regions of the body may be analyzed similarly.

At block 230, an imaging time series begins. At a first time point, t0, the energy emitted from the target medium is measured by various detectors positioned about a boundary of the target medium (block 240). The energy may originate within the target medium, e.g., as thermal energy, or may be emitted into the target medium from energy sources. For example, near infrared light energy may be used. Such energy sources may be positioned about the boundary of the target medium as discussed. At block 250, the system equation for the target medium (eqn (7)) can be solved using the weight matrix W of the reference medium and the measured energy to obtain the target medium properties (eqn. 8b). This is achieved by back-substituting values of the measured energy emerging from the target medium into the system equation. The weight matrix can be provided for an initial point in the time series by solving the system equation, without repeatedly calculating the weight matrix for subsequent points in the time series. Moreover, the weight matrix can be calculated for the initial time point at the time of imaging, or pre-calculated before the time of the imaging, e.g., by storing a library of weight matrices for different references media. Then, at the time of imaging, one of the pre-calculated weight matrices can be selected for immediate use in the system equation. At block 260, images can be optionally produced from the target medium properties using known techniques, e.g., for display on a computer monitor. At block 270, if the current point is the last point in the time series, the time series is ended (block 280).

If there are additional points in the time series, a further measurement is made of the emitted energy from the target medium at the next time point. At block 250, the system equation can be solved using the weight matrix that has previously been provided, thus avoiding the need to calculate the weight matrix for each point in the time series. Or, the weight matrix can be reused for a number of time points and recalculated for successive groups of time points. This approach, which is based on the fact that changes in the target medium during the time series are not typically gross, results in significant computational savings that enables real-time imaging. The processing occurs accordingly for each point in the time series until the time series has ended (block 280).

Note that the computer 102 of FIG. 1 may be programmed to perform the desired steps using techniques known to those skilled in the art. Moreover, the computer 102 may have memory elements for long-term and short-term data storage. For example, a long-term memory element may be used for storing a library of weight matrices that correspond to different reference mediums, as discussed.

In sum, in this disclosure we have recognized that because of the inherent stability of solutions obtained from the Normalized Difference Method, a variety of computation-saving techniques and stability-adding techniques can be introduced to provide for fast, accurate solutions of a time series of images involving large scale 3D problems.

The techniques are generally applicable to the use of essentially any energy source (e.g., electromagnetic, acoustic, fluorescence, bioluminescence, chemiluminescence, thermal, and the like), regardless of whether the energy is emitted into the target medium or generated within the target medium, and on any scattering medium (e.g., body tissues, oceans, foggy atmospheres, earth strata, industrial materials), so long as diffusive-type mechanisms are the principal means for energy transport through the medium. Fluorescence, bioluminescence, chemiluminescence, and thermal energy typically are generated from within a target medium. One example application is performing thermal imaging of an embryo.

The invention has been described herein with reference to particular exemplary embodiments. Certain alterations and modifications may be apparent to those skilled in the art, without departing from the scope of the invention. The exemplary embodiments are meant to be illustrative, not limiting of the scope of the invention, which is defined by the appended claims.

What is claimed:

1. A method for obtaining a time series of tomographic images of a target medium from an imaging apparatus, wherein source-detector pairs are positioned about a boundary of the target medium, and, in each source-detector pair, for different points in the time series, the source emits energy into the target medium and the detector measures the energy emerging from the target medium after passage therethrough, comprising:

selecting a reference medium;

providing a weight matrix describing an influence that volume elements of the reference medium have on energy traveling from sources to detectors in source-detector pairs of the reference medium, wherein said detectors measure an intensity of scattered energy;

transforming said weight matrix to reduce a dimension of said weight matrix employing a weight transformation technique, wherein an M×N matrix is transformed to an M×M matrix by said transforming, wherein N is a number of nodes comprising a finite element mesh and wherein M is the number of said source-detector pairs; and for the different points in the time series, solving a system equation for the target medium to determine properties of volume elements of the target medium that correspond to the volume elements of the reference medium based on the weight matrix and the energy emerging at the detectors of the target medium, wherein one or more of the properties of volume elements is employed at least for providing a time series of tomographic images of a target medium.

2. The method of claim 1, further comprising:
storing the weight matrix in memory for use in solving the system equation for at least some of the different points in the time series.

3. The method of claim 1, wherein:
solving the system equation comprises decomposing the weight matrix, and back-substituting values of the measured energy emerging from the target medium into the system equation for the different points in the time series.

4. The method of claim 1, wherein:
solving the system equation comprises decomposing the weight matrix using at least one of singular value decomposition and direct matrix decomposition.

5. The method of claim 1, wherein:
solving the system equation comprises transforming the weight matrix to reduce its dimensions.

6. The method of claim 1, wherein:
solving the system equation comprises scaling row vectors of the weight matrix.

7. The method of claim 1, wherein:
the properties of the volume elements of the target medium comprise at least one of scattering and absorption properties.

8. The method of claim 1, wherein:
the reference medium has at least one of scattering and absorption properties substantially similar to the properties of the target medium.

9. The method of claim 1, wherein:
the reference medium has a boundary with boundary conditions that are substantially similar to boundary conditions of the boundary of the target medium.

10. The method of claim 1, wherein:
the volume elements of the reference medium are formed by dividing the reference medium into a grid of contiguous, non-overlapping sections.

11. The method of claim 1, wherein:
the system equation of the reference medium comprises a perturbation equation.

12. The method of claim 1, wherein:
the target medium and reference medium comprise analogous tissue regions in an animal.

13. The method of claim 1, wherein:
the determined properties of the volume element of the target medium are used to provide the time series of tomography images substantially in real-time.

14. The method of claim 1, wherein:
the target medium comprises a turbid, scattering medium.

15. The method of claim 1, wherein:
the energy comprises near infrared light.

16. The method of claim 1, wherein:
the weight matrix is estimated.

17. The method of claim 1, wherein:
the weight matrix is obtained from a storage area of weight matrices that are correlated with different reference media.

18. The method of claim 1, wherein:
the source-detector pairs of the reference medium are positioned about a boundary of the reference medium in correspondence with the source-detector pairs positioned about the boundary of the target medium.

19. The method of claim 1, wherein the system equation includes at least Rytov approximation formulation.

20. The method of claim 1, wherein the system equation includes at least Born approximation formulation.

21. The method of claim 1, wherein the system equation is solved for at least some of the different points in the time series without repeatedly calculating the weight matrix.

22. A method for obtaining a time series of tomographic images of a target medium from an imaging apparatus, wherein source-detector pairs are positioned about a boundary of the target medium, and, in each source-detector pair, for different points in the time series, the source emits energy into the target medium and the detector measures the energy emerging from the target medium after passage therethrough, comprising:
selecting a reference medium;
providing a weight matrix describing an influence that volume elements of the reference medium have on energy traveling from sources to detectors in source-detector pairs of the reference medium, wherein said detectors measure an intensity of scattered energy; and
for the different points in the time series, solving a system equation for the target medium to determine properties of volume elements of the target medium corresponding to the volume elements of the reference medium by:
decomposing the weight matrix using at least one of singular value decomposition and direct matrix decomposition;
transforming the weight matrix to reduce its dimensions employing a weight transformation technique, wherein an M×N matrix is transformed to an M×M matrix by said transforming, wherein N is a number of nodes comprising a finite element mesh and wherein M is the number of said source-detector pairs; and
back-substituting values of the measured energy emerging from the target medium into the system equation for the different points in the time series,
wherein one or more of the properties of volume elements is employed at least for providing a time series of tomographic images of a target medium.

23. The method of claim 22, wherein the system equation is solved for at least some of the different points in the time series without repeatedly calculating the weight matrix.

24. A method for obtaining a time series of images of a target medium from an imaging apparatus, comprising:
positioning detectors about a boundary of the target medium for measuring energy that emerges from the target medium at different points in the time series, wherein the energy originates within the target medium;
selecting a reference medium;
providing a weight matrix describing an influence that volume elements of the reference medium have on energy originating within the reference medium and emerging from the reference medium at detectors positioned about a boundary of the reference medium, wherein said detectors measure an intensity of scattered energy;
decomposing the weight matrix using at least one of singular value decomposition and direct matrix decomposition employing a weight transformation technique, wherein an M×N matrix is transformed to an M×M matrix by said transforming, wherein N is a number of nodes comprising a finite element mesh and wherein M is the number of said source-detector pairs, wherein a dimension of the weight matrix is reduced by said decomposition of said weight matrix; and for the different points in the time series, solving a system equation for the target medium to determine properties of volume elements of the target medium corresponding to the volume elements of the reference medium based on the weight matrix and the energy emerging at the detectors of the target medium, wherein one or more of the properties of volume elements is employed at least for providing a time series of tomographic images of a target medium.

25. The method of claim 24, wherein:
the energy emerging from the target medium comprises at least one of fluorescence, bioluminescence, chemiluminescence, and thermal energy.

26. The method of claim 24, wherein:
solving the system equation comprises decomposing the weight matrix, and back-substituting values of the measured energy emerging from the target medium into the system equation for the different points in the time series.

27. The method of claim 24, wherein:
solving the system equation comprises decomposing the weight matrix using at least one of singular value decomposition and direct matrix decomposition.

28. The method of claim 24, wherein:
solving the system equation comprises transforming the weight matrix to reduce its dimensions.

29. The method of claim 24, wherein:
solving the system equation comprises scaling row vectors of the weight matrix.

30. The method of claim 24, wherein the system equation is solved for at least some of the different points in the time series without repeatedly calculating the weight matrix.

31. A method for obtaining a time series of images of a target medium from an imaging apparatus, comprising:
positioning detectors about a boundary of the target medium for measuring energy that emerges from the target medium at different points in the time series, wherein the energy originates within the target medium;
selecting a reference medium;
providing a weight matrix describing an influence that volume elements of the reference medium have on energy originating within the reference medium and emerging from the reference medium at detectors positioned about a boundary of the reference medium, wherein said detectors measure an intensity of scattered energy; and
for the different points in the time series, solving a system equation for the target medium to determine properties of volume elements of the target medium corresponding to the volume elements of the reference medium by:
decomposing the weight matrix using at least one of singular value decomposition and direct matrix decomposition;
transforming the weight matrix to reduce its dimensions employing a weight transformation technique, wherein an M×N matrix is transformed to an M×M matrix by said transforming, wherein N is a number of nodes comprising a finite element mesh and wherein M is the number of said source-detector pairs; and
back-substituting values of the measured energy emerging from the target medium into the system equation for the different points in the time series,
wherein one or more of the properties of volume elements is employed at least for providing a time series of tomographic images of a target medium.

32. The method of claim 31, wherein the system equation is solved for at least some of the different points in the time series without repeatedly calculating the weight matrix.

* * * * *

UNITED STATES PATENT AND TRADEMARK OFFICE
CERTIFICATE OF CORRECTION

| | | |
|---|---|---|
| PATENT NO. | : 7,616,984 B2 | Page 1 of 1 |
| APPLICATION NO. | : 10/408511 | |
| DATED | : November 10, 2009 | |
| INVENTOR(S) | : Barbour et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1825 days.

Signed and Sealed this

Nineteenth Day of October, 2010

David J. Kappos
*Director of the United States Patent and Trademark Office*